United States Patent
Tachino et al.

(10) Patent No.: US 6,190,611 B1
(45) Date of Patent: Feb. 20, 2001

(54) HARDNESS INDICATOR

(75) Inventors: Kazuhiro Tachino; Yoshitami Tsubota; Sadatoshi Takechi, all of Matsuyama; Junichi Nakajima, Hojo; Masazumi Yamashita, Matsuyama; Katsufumi Isshiki, Matsuyama; Takeshi Fukumura, Matsuyama; Yuuji Ukena, Matsuyama, all of (JP)

(73) Assignees: Miura Co., LTD.,; Miura Institute of Research & Development Co., Ltd., both of Matsuyama (JP)

( * ) Notice: Under 35 U.S.C. 154(b), the term of this patent shall be extended for 0 days.

(21) Appl. No.: 09/141,370

(22) Filed: Aug. 27, 1998

(30) Foreign Application Priority Data

Aug. 27, 1997 (JP) .................................. 9-247829

(51) Int. Cl.⁷ .................................. G01N 33/20
(52) U.S. Cl. .............................. 422/61; 436/74; 436/166; 436/79; 73/78
(58) Field of Search .................. 436/73, 74, 79, 436/166, 6; 73/78; 422/61

(56) References Cited

U.S. PATENT DOCUMENTS

| 3,159,586 | * | 12/1964 | Wildenhayn | 436/79 |
| 3,240,717 | * | 3/1966 | Johnson | 436/79 |
| 3,368,969 | | 2/1968 | Palen . | |
| 3,496,113 | | 2/1970 | Platte . | |
| 3,697,224 | | 10/1972 | Means . | |
| 3,895,913 | | 7/1975 | Bockowske et al. . | |
| 4,205,953 | * | 6/1980 | Miller | 436/79 X |
| 4,205,955 | | 6/1980 | Sloat . | |

FOREIGN PATENT DOCUMENTS

| 1125682 | * | 3/1962 | (DE) | 436/79 |
| 48-102694 | * | 12/1973 | (JP) . | |
| 51-150392 | * | 12/1976 | (JP) . | |
| 2-82160 | * | 3/1990 | (JP) . | |

OTHER PUBLICATIONS

R. L. McCullough et al. Chem. Abstr, Jan. 1970, 72, 18133s.*
L. Wunsch Clin. Chim. Acta 1970, 30, 157–163.*

* cited by examiner

*Primary Examiner*—Arlen Soderquist
(74) *Attorney, Agent, or Firm*—Birch, Stewart, Kolasch & Birch, LLP.

(57) ABSTRACT

A harness indicator is highly reactive to a trace amount of $Ca^{2+}$, and is slow to degrade in a high temperature environment of greater than 50° C. In one embodiment, the hardness indicator contains EBT, a pH buffer, and a masking agent as main components, and an admixture of Mg-EDTA. In another embodiment, the hardness indicator contains EBT, a pH buffer, and a masking agent as main components, and an admixture of anhydrous Mg-EDTA. In another embodiment, the hardness indicator contains EBT, a pH buffer, and a masking agent as main components, and an admixture of anhydrous Mg-EDTA and potassium sorbate. In a further embodiment, the hardness indicator contains EBT, a pH buffer, and a masking agent as main components, and an admixture of Mg-EDTA and potassium sorbate. In a further embodiment, the hardness indicator contains EBT, a pH buffer, and a masking agent as main components, and an admixture of potassium sorbate.

18 Claims, No Drawings

HARDNESS INDICATOR

BACKGROUND OF THE INVENTION

1. Field of the Invention

The present invention relates to a novel hardness indicator for detecting a hardness in a water sample.

2. Description of Related Art

Generally, city water is unsuitable for use as boiler feed water or food processing water because city water contains various kinds of impurities (e.g., hardness components such as calcium and magnesium), even if the water is fit for drinking.

Direct use of such city water as boiler feed water may cause scale deposition and/or corrosion. Therefore, it is usual practice to employ a water softening apparatus, a water deionizing apparatus, or the like thereby to provide water free of such impurities. In such a softening apparatus, for example, a strong acid cation exchange resin of Na type is used whereby hardness components ($Ca^{2+}$ and $Mg^{2+}$) of the raw water are replaced by $Na^+$ so that the water is changed into soft water. However, the apparatus poses a problem that due to degradation or insufficient regeneration of the ion exchange resin there may occur hardness leaks. Therefore, it is necessary to check treated water constantly to see that there are no hardness leaks.

In the case where the method employed for detecting such a leak is such that a hardness indicator is added to soft water, so that any such leak can be detected by a change in the color of the indicator, it is desirable that for facilitating visual detection of the change in color, such a color change appears in a reasonably pronounced way in reaction to the hardness leak, even when the leak is small.

In many cases, the main component of the hardness indicator is usually EBT (eriochrome black T), and an aqueous solution of the hardness indicator is colored blue within a pH range of from 8 to 10. However, the aqueous solution has a characteristic feature where it promptly turns red upon inclusion of $Mg^{2+}$. This characteristic feature is utilized for checking to see whether or not $Mg^{2+}$, i.e., a hardness component, is present in the soft water.

A hardness indicator of this type reacts on $Ca^{2+}$ to form a water-soluble compound. However, as compared with a compound formed through its reaction on $Mg^{2+}$, this compound is unstable and the change in its color is rather dull.

When such a hardness indicator is allowed to stand in a high temperature environment of greater than 50° C. as in a boiler room, EBT is oxidized so that the hardness indicator degrades.

As described above, while EBT is highly reactive with $Mg^{2+}$ to exhibit a sharp change in its color, an change in its color as a reaction on $Ca^{2+}$ is dull. As such, the sensitivity of EBT differs on the order of over 10 times depending upon the conditions. Usually, however, the concentrations of $Ca^{2+}$ and $Mg^{2+}$ in the raw water are such that the concentration of $Ca^{2+}$ is far much greater than that of the other, say, on the order of from about 3 times to 10 times the concentration of $Mg^{2+}$, though their respective concentrations differ from district to district. Therefore, the possibility of $Ca^{2+}$ leak into the soft water is far much higher than the possibility of $Mg^{2+}$ leak and this requires early detection of $Ca^{2+}$ hardness leaks. Further, a quick reaction B required on trace amounts of $Ca^{2+}$.

Another problem is that, as already stated, a hardness indicator is liable to faster degradation under high-temperature conditions. Therefore, in order that the hardness indicator may maintain its performance quality, it is necessary to slow down the degradation of the hardness indicator.

SUMMARY OF THE INVENTION

This invention has been developed for solving above mentioned problems and provides, in a first aspect thereof, a hardness indicator comprising EBT, a pH buffer, and a masking agent as main components, and an admixture of Mg-EDTA. According to its second aspect, the invention provides a hardness indicator comprising EBT, a pH buffer, and a masking agent as main components, and an admixture of anhydrous Mg-EDTA. In a third aspect of the invention, there is provided a hardness indicator in accordance with the second aspect which further comprises an admixture of a reducing agent such as potassium sorbate. In its fourth aspect, the invention provides a hardness indicator comprising EBT, a pH buffer, and a masking agent as main components, and an admixture of Mg-EDTA and a reducing agent such as potassium sorbate. In its fifth aspect, the invention provides a hardness indicator comprising EBT, a pH buffer, and a masking agent as main components, and an admixture of a reducing agent such as potassium sorbate.

DETAILED DESCRIPTION OF THE PREFERRED EMBODIMENTS

Preferred embodiments of the invention will now be described in detail. In the invention, EBT is used as a main component of the hardness indicator. To the EBT are added a masking agent and a non-aqueous triethanolamine as a pH buffer, and the mixture is dissolved in ethylene glycol, a non-aqueous solvent, whereby a base for the hardness indicator is obtained.

Then, a commercially available Mg-EDTA is added to the base for the hardness indicator, so that a hardness indicator which sensitively reacts on a trace amount of $Ca^{2+}$ can be obtained. The commercially available Mg-EDTA is in the form of a hydrate containing a water molecule. The water molecule reacts with EBT to cause hydrolysis to thereby degrade the hardness indicator. Under ambient temperature conditions of not more than 50° C., the reaction rate in such hydrolysis is very low. Materials such as triethanolamine and ethylene glycol are non-aqueous and do not involve the problem of EBT hydrolysis. Therefore, the hardness indicator is little liable to degradation and poses no problem from the viewpoint of practical use.

Under ambient temperature conditions of greater than 50° C., the reaction rate in the process of the aforesaid hydrolysis is comparatively high, so that the degradation of the hardness indicator accelerates. Therefore, water molecules are removed from the commercial Mg-EDTA, and the resulting anhydrous is added to the base for the hardness indicator. In this way, a hardness indicator can be obtained which is slow to degrade under ambient temperature conditions of greater than 50° C.

When the base for the hardness indicator is loaded with potassium sorbate as a reducing agent, a hardness indicator can be obtained which is slow to degrade under ambient temperature conditions of greater than 50° C.

The above described modes of carrying out the invention may be carried out simultaneously. In that case, a hardness indicator can be obtained which is slow to degrade and which sensitively reacts on a trace amount of $Ca^{2+}$. That is, the desired hardness indicator can be obtained when the base for the hardness indicator is loaded with anhydrous Mg-EDTA commercially available Mg-EDTA hydrate, and with potassium sorbate.

EXAMPLES

The following examples are given to illustrate the present invention in further detail. In the invention, EBT is a main component of the hardness indicator. The main component EBT reacts on metallic salt in such a way that its color changes from blue to red to indicate the presence of metallic salt. The change in color appears pronouncedly in a pH range of from 8 to 10. In this invention, therefore, a pH buffer for keeping the pH of the sample solution within the pH range of from 8 to 10, and the masking agent for a color indicator are required. When, for example, triethanolamine is used in this connection, the functions of both pH buffer and masking agent can be performed simultaneously, whereby the number of necessary components are according reduced.

The solvent used in the hardness indicator may be ethylene glycol, for example. In preparing the hardness indicator, the EBT and triethanolamine are dissolved in the ethylene glycol. The resulting solution serves as the base for the hardness indicator.

In the present invention, various components are added to the base for the hardness indicator in manner as hereinbelow described, whereby the hardness indicator is obtained in its complete form.

First, a First Example will be described. In the First Example, commercially available Mg-EDTA is added to the base for the hardness indicator. When the hardness indicator is put dropwise into the sample solution, reaction occurs in manner as shown by formulas 1 and 2.

$$Ca^{2+} + Mg\text{-}EDTA \rightarrow Mg^{2+} + Ca\text{-}EDTA \quad \text{Formula 1}$$

$$Mg^{2+} + EBT \rightarrow Mg\text{-}EBT \quad \text{Formula 2}$$

In Formula 1, $Ca^{2+}$ in the sample solution is replaced by an equimolar amount of $Mg^{2+}$, and is then reacted with EBT as in Formula 2 so that a sensitive color change will occur with respect to its color.

Next, a Second Example will be explained. In the Second Example, commercially available Mg-EDTA is used as in the First Example, but this Mg-EDTA is sold usually in the form of a hydrate containing a water molecule. If the Mg-EDTA is used directly as such in preparing a hardness indicator, the water molecule and aforesaid EBT react with each other (to be hydrolyzed) in a high temperature environment of greater than 50° C., and this may be a cause of early degradation of the hardness indicator. Therefore, in case that commercially available Mg-EDTA is used, the Mg-EDTA is heated at 120° C. so as to be dehydrated before it is used in the preparation of the hardness indicator. Through this treatment the degradation of the hardness indicator slows down under high temperature conditions of greater than 50° C.

The reactions which occur when the hardness indicator of the Second Example is put dropwise onto the sample solution are same as shown by Formulas 1 and 2. Therefore, a detailed description of the Second Example is omitted.

Next, a Third Example will be explained. In the Third Example, a reducing agent, e.g., potassium sorbate, is added to the hardness indicator. The potassium sorbate functions to slow down the degradation of the EBT due to oxidization thereof under high temperature conditions of greater than 50° C.

In a Fourth Example, components of the Second and Third Examples are used in combination to provide the desired hardness indicator. That is, after the water molecule is removed from the commercially available Mg-EDTA, the anhydrous Mg-EDTA is added to the base for the hardness indicator. Further, potassium sorbate is added as a reducing agent, whereby a hardness indicator which is slower to degrade can be obtained.

As described above, according to this invention, the hardness indicator comprises EBT, a pH buffer, and a masking agent as main components, and an admixture of Mg-EDTA. Therefore, the hardness indicator is highly reactive to a trace amount of $Ca^{2+}$ in the water to be treated. In one embodiment, the hardness indicator comprises EBT, a pH buffer, and a masking agent as main components, and an admixture of anhydrous Mg-EDTA prepared by removing a water molecule from Mg-EDTA hydrate. Therefore, the hardness indicator is quickly reactive to a trace amount of $Ca^{2+}$ in the water to be treated and is slow to degrade even under high-temperature environment conditions of not less than 50° C.

In another embodiment, the hardness indicator includes an admixture of a reducing agent such as potassium sorbate; therefore, the hardness indicator can quickly react on a trace amount of $Ca^{2+}$ in the water to be treated and is slower to degrade under high-temperature environment conditions of greater than 50° C.

What is claimed is:

1. A non-aqueous hardness indicator comprising
   EBT,
   a pH buffer,
   a masking agent,
   Mg-EDTA, and
   a non-aqueous solvent.
2. The hardness indicator as set forth in claim 1, wherein the solvent comprises ethylene glycol.
3. The hardness indicator as set forth in claim 1, wherein the pH buffer comprises triethanolamine.
4. The hardness indicator as set forth in claim 2, wherein the pH buffer buffers in a pH range of 8–10.
5. A non-aqueous hardness indicator comprising
   EBT,
   a pH buffer,
   a masking agent,
   anhydrous MG-EDTA, and
   a non-aqueous solvent.
6. The hardness indicator as set forth in claim 5, further comprising potassium sorbate.
7. The hardness indicator as set forth in claim 5, wherein the solvent comprises ethylene glycol.
8. The hardness indicator as set forth in claim 5, wherein the pH buffer comprises triethanolamine.

9. The hardness indicator as set forth in claim 5, wherein the anhydrous Mg-EDTA is obtained by heating Mg-EDTA hydrate to 120° C.

10. The hardness indicator as set forth in claim 5, wherein the pH buffer buffers in a pH range of 8–10.

11. A non-aqueous hardness indicator comprising EBT,
a pH buffer,
a masking agent,
Mg-EDTA,
potassium sorbate, and
a non-aqueous solvent.

12. The hardness indicator as set forth in claim 11, wherein the solvent comprises ethylene glycol.

13. The hardness indicator as set forth in claim 11, wherein the pH buffer comprises triethanolamine.

14. The hardness indicator as set forth in claim 11, wherein the pH buffer buffers in a pH range of 8–10.

15. A non-aqueous hardness indicator comprising
EBT,
a pH buffer,
a masking agent,
potassium sorbate, and
non-aqueous solvent.

16. The hardness indicator as set forth in claim 15, wherein the solvent comprises ethylene glycol.

17. The hardness indicator as set forth in claim 15, wherein the pH buffer comprises triethanolamine.

18. The hardness indicator as set forth in claim 15, wherein the pH buffer buffers in a pH range of 8–10.

* * * * *